United States Patent [19]

Leslie et al.

[11] 3,977,083
[45] Aug. 31, 1976

[54] DENTAL INSTRUMENT

[76] Inventors: Norman Leslie, 17015 Escalon Drive; Ben A. Otsap, 5437 Newcastle Ave., both of Encino, Calif. 91316

[22] Filed: Feb. 5, 1974

[21] Appl. No.: 440,154

[52] U.S. Cl............................................. 32/58; 32/27
[51] Int. Cl.²........................................... A61C 3/06
[58] Field of Search .............. 32/58, 59, 26, 27, 28; 128/214 F

[56] References Cited
UNITED STATES PATENTS

| 2,400,912 | 5/1946 | Britt et al.............................. 32/59 |
| 2,442,033 | 5/1948 | Brantly et al.......................... 32/28 |
| 2,697,878 | 12/1954 | Oberley................................. 32/59 |
| 2,738,528 | 3/1956 | Fridge, Sr............................. 32/28 X |
| 2,838,837 | 6/1958 | Terry..................................... 32/28 |
| 2,857,671 | 10/1958 | Nelson................................... 32/59 |
| 3,195,537 | 7/1965 | Blasi...................................... 32/27 |
| 3,389,468 | 6/1968 | Lewis et al............................. 32/59 |
| 3,439,422 | 4/1969 | Doeden et al......................... 32/26 |
| 3,599,333 | 8/1971 | Muhler................................... 32/59 |
| 3,640,276 | 2/1972 | Dancy, Jr.......................... 128/214 F |
| 3,691,636 | 9/1972 | Deuschle................................ 32/58 |
| 3,775,849 | 12/1973 | Condon.................................. 32/59 |
| 3,789,462 | 2/1974 | Reich..................................... 32/59 |
| 3,826,004 | 7/1974 | Graceffo................................ 32/58 |

*Primary Examiner*—Louis G. Mancene
*Assistant Examiner*—Jack Q. Lever
*Attorney, Agent, or Firm*—Matthew P. Lynch

[57] ABSTRACT

An improved dental instrument for use in cleaning teeth, the instrument having a polishing cup with a self-contained abrasive and a system for automatically supplying a cooling fluid to the polishing cup when the cup is rotated; the cooling fluid serving the additional purpose of lubricating the cup driving mechanism, thereby eliminating the need of packing the driving mechanism in grease and allowing the instrument to be sterilized between uses.

6 Claims, 9 Drawing Figures

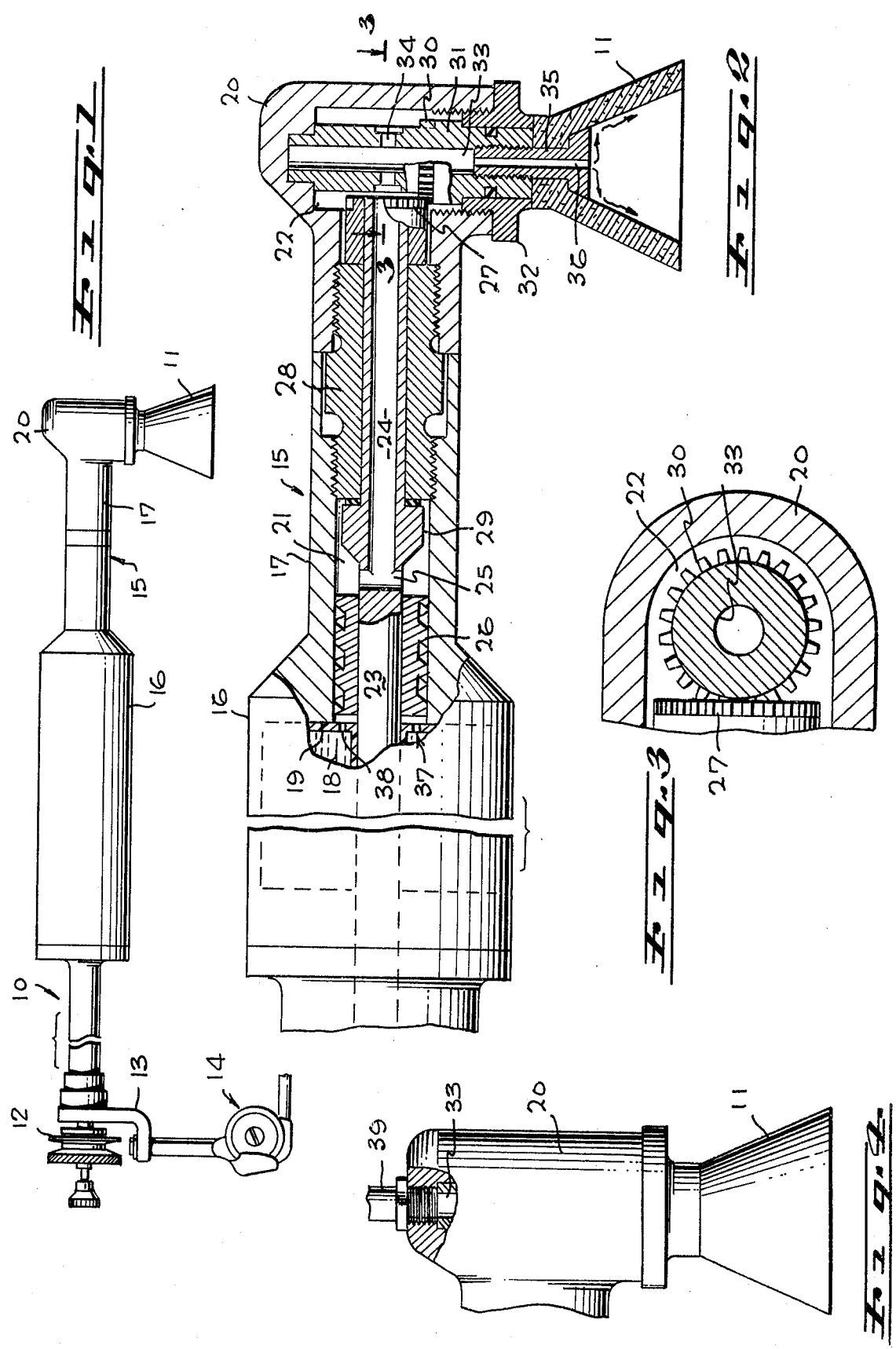

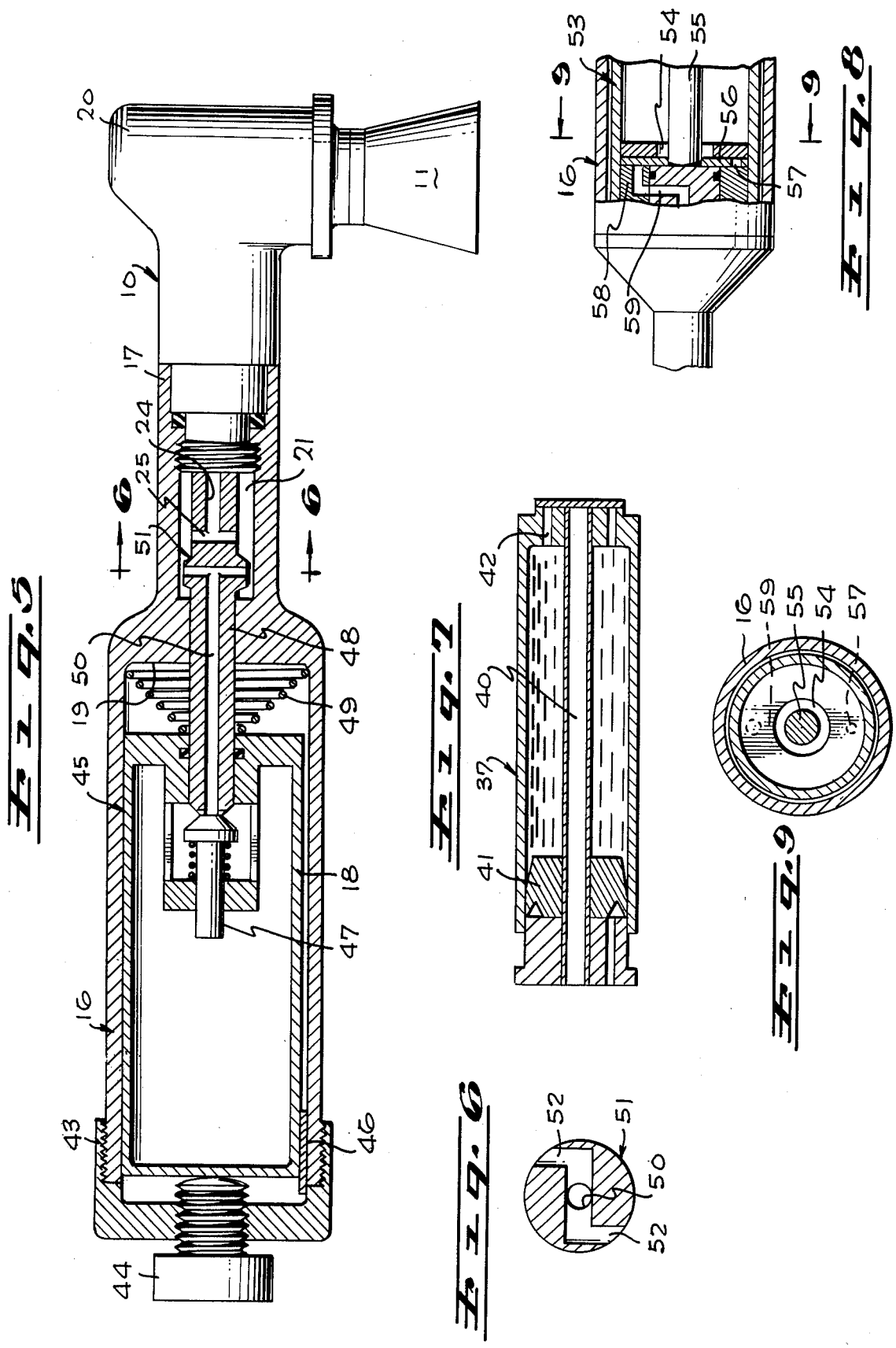

DENTAL INSTRUMENT

BACKGROUND OF THE INVENTION

This invention relates to a novel dental hand piece for utilization in the cleaning of teeth.

The most common method in widespread use today, among dentists, for the cleaning of teeth consists of the utilization of an abrasive polishing paste in combination with a dental handpiece having a rotatable elastomeric polishing or prophy cup secured thereto. The paste is normally carried or disposed in a relatively small jar or container and the polishing cup is manually dipped into the supply of paste for coating of the cup with the polishing or cleaning material. The coated polishing cup is then applied to the surface of the teeth and the handpiece is actuated by the dentist's usual power equipment for rotating rotating the cup. This procedure of dipping the polishing cup into the supply of paste and applying the coated cup to the surface of the teeth is not only time-consuming for the dentist but also the normal rotational speed of the coated cup causes the paste to be thrown from the cup due to centrifugal force. As a result, the polishing of the teeth is unduly time-consuming because of the constant dipping and the visual obstruction of the tooth being cleaned by the paste and of discomfort to both the patient and the dentist due to the paste being thrown around.

In addition to the aforementioned disadvantages, the same dental handpiece is used over and over for all patients, thereby transferring gems from the mouth of one patient to the mouth of another. Obviously, it is a very unsanitary process to place the same dental instrument into the mouths of different patients without sterilizing the instrument between patients. Most dentists recognize that such a procedure is at best unsanitary and fraught with danger but they have no choice in the matter since the head of the dental instrument, into which the polishing cup is inserted, has a number of gears therein which are caused to rotate and the gears are packed in grease and sealed. If the dentist tried to sterilize the instrument the grease would break down and not perform its lubricating function and within a short period of time the gears would jam, thereby rendering the instrument inoperable.

SUMMARY OF THE INVENTION

The present invention overcomes the aforementioned problems by providing a dental instrument that can be used for the cleaning and polishing of teeth without the need for constant dipping in a separate cup of paste and the gears of which are lubricated by the same fluid that cools the tooth being cleaned. The invention consists of a polishing cup which is rotably secured to the head of the instrument; the cup is a self-contained polishing tool in that there is impregnated into the elastomeric material from which the cup is constructed an abrasive material. By providing a polishing cup which has its own supply of abrasive material the utilization of a separate supply of paste is eliminated. Additionally, the driving gears within the head of the instrument are lubricated by the fluid which is caused to pass therethrough into the polishing cup, thereby eliminating the necessity of packing the gears in grease and consequently allowing the instrument to be sterilized between patients. The fluid is supplied to the cup from an independent source which is secured to the instrument and provision is made to regulate the flow of the fluid in proportion to the rotating speed of the cup so that as the cup's speed increases the amount of fluid provided to cool the tooth being cleaned is increased.

BRIEF DESCRIPTION OF THE DRAWING

FIG. 1 is a side elevation of a dental instrument;

FIG. 2 is a side elevation partially in section of one embodiment of the present invention;

FIG. 3 is a sectional plan view along line 3—3 of FIG. 2; and

FIG. 4 is a fragmentary view of an alternate embodiment of the present invention.

FIG. 5 is a side elevation partially in section of an alternate embodiment of the present invention.

FIG. 6 is a sectional view along line 6—6 of FIG. 5.

FIG. 7 is a side elevation in section of a supply cartridge utilized in the present invention.

FIG. 8 is a fragmentary view of an alternate fluid metering system of the present invention FIG. 9 is a sectional view along line 9—9 of FIG. 8.

DESCRIPTION OF THE PREFERRED EMBODIMENT

Referring now to the drawings, wherein the like reference numbers designate like or corresponding parts throughout the several views, there is shown in FIG. 1 a conventional dental instrument 10 to which the present invention may be incorporated as a built-in part thereof or combined therewith as an attachment. In FIG. 1 there is shown the dental instrument 10 having a polishing cup 11 which is adapted to be rotated by a pulley 12. The instrument 10 is supported by a bracket 13 which extends from an articulated frame 14 on which is carried means for rotating the pulley 12 in a well known manner.

While a drive train as shown in FIG. 1 is typical with regard to dental instrument it is contemplated by the present invention that the dental instrument 10 can be made into a portable instrument which would have an independent drive means. An alternate gas driven model is illustrated in FIG. 5 and is described in detail hereinafter. However in addition to the embodiments illustrated in the various figures it also is intended that a dental instrument 10 which is driven electrically is encompassed by the present invention. In such an electrically driven instrument, a battery and an electrical motor would be incorporated within the instrument and the instrument would be adapted to be pluged into an electrical source in order to either recharge the battery or to directly drive the motor. An illustration and detailed description of such an arrangement has not been provided herein since such a drive means is well known in the art to which this invention pertains and in the interest of brevity and clarity it is not warrented.

The instrument 10 of FIG. 2 basically consists of a hollow substantially tubular handpiece 15 having a body portion 16 and a head portion 17. The body portion 16 has a chamber 18 extending therethrough and terminating at an annular shoulder 19 adjacent the head portion 17. The head portion 17 consists generally of a tubular member having an enlarged end 20, the tubular member of the head portion has a diameter smaller than the diameter of the body portion 16. Disposed longitudinally through the tubular member of the head portion 17 and terminating adjacent the enlarged end 20 is a channel 21 which is coaxial to the chamber 18. Extending through one end of the enlarged end 20 and terminating adjacent its opposite end is an aperture 22 which intersects the channel 21 in an orientation normal thereto and extends therebeyond to its termination point.

Extending through the chamber 18 and the channel 21 in coaxial longitudinal alignment to the body portion 16 and the head portion 17 is a shaft 23. The shaft 23 is secured on one end to a driving means and terminates in complementary relationship to the aperature 22 in the enlarged end 20 and is adapted to be rotated by the driving means. Disposed within the shaft 23 from its end adjacent the aperature 22 to a point intermediate the ends of the head portion 17 is an orifice 24, which orifice is coaxial to the channel 21. Radiating outwardly from the end of the orifice 24 which terminates intermediate the ends of the head portion 17 are a plurality of vents 25 which extend through the shaft 23 into communication with the channel 21, thereby providing a passageway from the channel 21 to the aperature 22.

Secured to the shaft 23 within the channel 21 adjacent to the chamber 18 and extending along the shaft to a point adjacent the vents 25 is a spiral screw pump 26. The screw pump 26 because of its attachment to the shaft 23, is adapted to rotate in conjunction with the shaft and is configured to draw material from the chamber 18 through the pump into the channel 21 adajacent to the vents 25. A bevel gear 27 is secured to the end of the shaft 23 along its end so that a portion of the bevel gear 27 extends into the aperature 22, the axis of rotation of the bevel gear 27 is coaxial to the axis of rotation of the shaft 23 and the screw pump 26. The shaft 23 is supported along its length within the channel 21 by a bushing 28 which has an inner diameter slightly larger than the outer diameter of the shaft 23 so that the shaft is permitted to rotate within the bushing 28, but prevented from bending. The bushing 28 can be constructed from any one of many materials which have a low coefficient of friction and a high strength.

The bushing 28 engages the shaft 23 along its length between the vents 25 and the bevel gear 27 and is adapted to be rigidly secured in the channel 21 in order that the bushing will remain in a fixed position while the shaft 23 is allowed to rotate. The shaft 23 has an enlarged portion 29 intermediate the vents 25 and the bushing 28 to longitudinally locate the shaft 23 in a fixed position in order to ensure that the bevel gear 27 engages and remains in engagement with a second bevel gear 30 which is disposed within the aperature 22 in normal relationship to the bevel gear 27. The bevel gear 30 may be secured to or be an integral part of an arbor 31 which is journaled within the aperature 22 in a perpendicular relationship to the shaft 23. The arbor 31 is adapted to be rotated in conjunction with the bevel gear 30 when the bevel gear 30 is caused to be rotated by the bevel gear 27 and the shaft 23. In effect, the bevel gear 27 is the driving gear and the second bevel gear 30 is the driven gear. A lock nut 32 is disposed within the open end of the aperature 22 and adapted to rotatably secure the arbor 31 within the aperature 22. Disposed longitudinally through the arbor 31 is an orifice 33, which orifice is intersected by a plurality of vents 34 which extend through the arbor 31 in coaxial complementary relationship to the orifice 24 of the shaft 23.

The polishing cup 11 has secured thereto a securing means 35 which is adapted to secure the cup 11 to the arbor 31 in a manner which allows the cup 11 to rotate in conjunction with the arbor 31 while allowing the cup 11 to be removed from the arbor for repair or replacement. The securing means 35 has an aperature 36 which extends thererthrough in coaxial alignment with orifice 33 of the arbor 31.

In operation, a polishing cup 11 having the desired abrasive rating, which can be regulated by the amount and mesh size of the pumice or other abrasive imbedded in the cup, is secured to the arbor 31. A cartridge 37 which has a channel 40 extending longitudinally therethrough is disposed within the chamber 18 so that the shaft 23 extends through the channel 40 of the cartridge 37. The cartridge 37 is filled with a fluid, such as glycerine, which has both cooling and lubricating characteristics and is provided with a pllurality of openings 38 which extend through the end of the cartridge 37 and allow the glycerine to flow from the cartridge into the channel 21. A typical cartridge 37 is shown in FIG. 7 from which it will be apparent that a piston 41 can be incorporated within the cartridge 37 to assist in the evacuation of the fluid contained therein. If desired the piston 41 can be biased towards the openings 38 by a spring (not shown) or a source of compressed gas or any other well known means. In FIG. 7 it will be noted that an additional opening 42 is located in the end wall of the cartridge 37 behind the piston 41 and if desired a pressure source can be incorporated within the dental handpiece 15 to supply a pressure to the backside of the piston 41 in order to move it forward. There are obviously many alternative methods of evacuating the fluid from the cartridge 37 such as a screw worm but since such means are well known in the art a detailed description will not be included herein. The operator, upon energizing the drive means, causes the shaft 23 to rotate, which in turn through the driving arrangement of the bevel gears 27 and 30 causes the arbor 31 and the polishing cup 11 to rotate. As the shaft 23 rotates the screw pump 26 draws the cooling fluid from the cartridge 37 and forces it into the channel 21 adjacent the vents 25. The fluid in the channel 21 is caused to enter the vents 25 and flow through the orifice 24 in the shaft 23 and exit into the aperature 22 of the enlarged end 20, by the pressure of the fluid behind it, by capillary action and other physical phenomena. Upon entering the aperature 22, the fluid passes around the arbor 31 and over the bevel gears 27 and 30, thereby lubricating and cooling the moving parts, and into the vents 34 of the arbor 31. The fluid entering the vents 34 passes through the orifice 33 of the arbor and aperature 36 of the polishing cup securing means 35 to enter into the polishing cup 11 where centrifugal force causes the fluid to spread evenly along the entire inner surface of the cup. As can be seen from the description of the operation of the instrument, the fluid is caused to pass from its supply source through the instrument itself into contact with all moving parts, thereby providing the necessary cooling and lubricating of the moving parts and especially the gearing arrangement and thence into the self-contained polishing cup where the same fluid which lubricates the gears is used to cool the teeth being cleaned. If desired the fluid used for the cooling and lubricating can have various medicinal or cosmetic additives dispersed therein, for example it might be advantageous to add a flavoring agent to the fluid or a floride solution so that in addition to providing a pleasant taste the teeth may be medically treated. Obviously the various types of additives that can be incorporated in the fluid supply are almost endless and an exhaustive recitation would serve no purpose.

FIG. 4 illustrates an alternate embodiment of the present invention, wherein a metering tube 39 is disposed in the closed portion of the enlarged end 20 in a manner such that the tube 39 is in communication with the orifice 33 of the arbor 31. In this embodiment the fluid is caused to pass through the tube 39 from a source (not shown) in a rate proportional to the rotational speed of the arbor and then pass through the orifice 33 and the aperature 36 into the polishing cup 11. A portion of the fluid is caused to pass outwardly through the vents 34 by centrifugal force and thereby coontact and lubricate the gears 27 and 30 and arbor 31. In such an embodiment it is not necessary to provide a cartridge 37, pump 26 or attendent passageways to take the fluid from the body of the instrument to the end 20.

An alternate embodiment of the dental instrument 10 wherein the cooling fluid is a gas is shown in FIG. 5. The dental instrument of this embodiment which is shown partially in section is of a unitary design in that it has a self-contained power, lubricating and cooling means. It will be noted that the enlarged end portion 20 has not been cut away, the reason being that the arrangement of parts therein is essentially the same as shown in FIG. 2 including the gearing arrangement.

In FIG. 5 the body portion 16 terminates in an open end to which is secured an end cap 43. The end cap 43 can be secured to the body portion 16 in any one of many known ways, the only restriction being that the end cap 43 should be easily removable and replaceable as desired. Disposed centrally through the end cap 43 and adapted to be longitudinally adjusted is a speed adjusting means 44 which in the illustrated embodiment is shown as a thumb screw threadably secured through the end cap. Disposed within the chamber 18 of the body portion 16 is a cartridge 45, the cartridge is maintained in a fixed position with regard to rotational movement by a detent 46 which is shown as a key disposed within the wall of the chamber 18 and adapted to mate with a longitudinal groove in the cartridge 45, however the detent can be a spring biased ball or any other mechanism which would prevent rotational movement.

The cartridge 45 differs from the cartridge 37 of FIG. 7 in that the cartridge 37 is adapted to contain and dispense a liquid while the cartridge 45 is adapted to contain and dispense a gas. In effect the cartridge 45 is similar to what is commonly known as a aerosol can in that a gas is contained therein under pressure and a valve is arranged in one end to provide a controlled release of the contained gas. When the cartridge 45 is inserted within the chamber 18 and the end cap 43 is secured to the body portion 16 the valve 47 is brought into abutment with the end of a shaft 48. When the speed adjusting means 44 is fully retracted the valve 47 of the cartridge 45 resides in its fully extended or closed position and the cartridge 45 is sealed and the gas contained therein is prevented from being released. When it is desired to release the gas the means 44 is caused to enter the chamber 18 where it contacts the sealed end of the cartridge and forces the valve 47 into contact with the end of the shaft 48. As the cartridge is forced further into the chamber the shaft 48 causes the valve 47 to retract thereby allowing the gas in the cartridge to be released. The further the cartridge 45 is forced into the chamber 18 by the means 44 the more the valve 47 is retracted by the shaft 48 and the greater the amount of gas that is released. When it is desired to terminate the flow of gas the means 44 is retracted from the chamber and the spring biased valve 47 returns to its sealing position. In other words the speed adjusting means 44 by regulating the depth of penetration of the cartridge 45 into the chamber regulates the opening of the valve 47 and consequently the volume of gas released. The cartridge 45 is biased towards the means 44 by a spring 49 which is positioned within the chamber 18 between the annular shoulder 19 and the cartridge 45 in surrounding disposition to the shaft 48.

The shaft 48 extends longitudinally through the head portion 17 and is adapted to drive the arbor 31 in the same manner as the shaft 23 of FIG. 2. The primary distinction between the shaft 48 and the shaft 23 is that the shaft 48 in addition to providing means for allowing the lubricating and cooling fluid to pass through the bevel gears into the cup 11 also has a self-contained driving means adapted to rotate the shaft in response to the release of gas from the cartridge 45. The shaft 48 has a longitudinal channel 50 which originates at its end which is in contact with the valve 47 and extends longitudinally through the shaft to a point within the channel 21 of the head portion 17. The channel 50 terminates at an enlarged portion of the shaft which serves as a turbine reaction wheel 51. The turbine wheel 51 is illustrated in greater detail in FIG. 6 wherein it can be seen to have a pair of opposed discharge vents 52 which radiate outwardly from the channel 50. Disposed between the turbine wheel and the enlarged end 20 the shaft 48 is provided with vents 25 interconnecting with a longitudinal orifice 24 in the same manner as shaft 23 of FIG. 2.

In operation the end cap 43 is removed and the cartridge 45 is inserted within the chamber 18. The end cap 43 is then replaced and the speed adjusting means 44 is screwed inwardly forcing the valve 47 into engagement with the end of the shaft 48. As the shaft 48 depresses the valve 47 the gas contained within the cartridge 45 is released and enters the channel 50 at a high velocity. The gas passes through the channel 50 into the turbine wheel 51 where it imparts a rotational force to the shaft 48 in a manner similar to a turbine as it exits through the discharge vents 52. The rotational movement developed by the turbine wheel 51 causes the shaft 48 to rotate which through its drive train causes the polishing cup 11 to rotate. The gas after exiting through the discharge vents 52 into the channel 21 is caused to enter the vents 25 and pass through the orifice 24 in the shaft 48 and exit into the aperature 22 of the enlarged end 20. Upon entering the aperature 22, the gas passes around the arbor 31 and over the bevel gears 27 and 30, thereby lubricating and cooling the moving parts and into the vents 34 of the arbor 31. The gas entering the vents 34 passes through the orifice 33 of the arbor and aperature 36 of the polishing cup securing means 35 to enter into the polishing cup 11 whereupon it impinges upon the tooth being cleaned and cools such tooth. It will be noted from the above description of its operation that the gas upon exiting from the turbine wheel 51 follows an identical path as the fluid in the operation of the embodiment of FIG. 2. It is well known that there are many inert gases which are capable of lubricating moving parts and of cooling such parts and any other elements that it may contact and therefore a complete recitation of such gases will not be presented, however one such gas would be nitrogen.

Another embodiment which can be adapted to work in conjunction with the embodiment of FIG. 2 is illustrated in FIG. 8 where there is shown a section of the body portion 16. Disposed within the chamber 18 of the body portion 16 is a cartridge 53 which can be filled with a lubricating and cooling fluid such as glycerine. Slidably disposed within the cartridge 53 is a piston (not shown) which can be biased by a spring or other means to cause the fluid within the cartridge to discharge through the orifice 54. Rotatably disposed through the cartridge 53 is a shaft 55 which has secured thereto adjacent the orifice 54 a metering disc 56. The metering disc 56 is of an annular construction and has an aperature 57, which aperature is not in alignment with the orifice 54. The disc 56 is adapted to rotate in conjunction with the shaft 55 and is positioned between the end of the cartridge 53 which contains the orifice 54 and the shoulder 19 of the body portion 16. An annular member 58 is fixedly disposed within the body portion 16 between the disc 56 and the shoulder 19, the member having a passageway 59 which is complementary to the aperature 57 of the disc 56 at one end and complementary to the vent 25 in the shaft 55 at its other end.

In operation, when the shaft 55 is rotated the disc 56 is caused to rotate in conjunction with the shaft, however if desired the disc 56 can be secured to the shaft 55 by a slight friction fit so that the disc will not have the same revolutions per minute (RPM) as the shaft but will have a predetermined amount of slippage which will cause the disc 56 to rotate at a lesser percentage of the shaft's rotation. Regardless of which arrangement is utilized, as the disc 56 rotates, the aperature 57 picks up a predetermined amount of fluid from the cartridge 53. As will be noted from FIG. 8, the disc 56 is spaced from the end of the cartridge 53 which contains the orifice 54 and as the fluid within the cartridge discharges through the orifice it flows into the space where the aperature 57 of the disc 56 picks up a metered portion. As the disc continues to rotate the aperature 57 comes into complementary relationship with the passageway 59 of the member 58 at which time the fluid is transferred from the aperature 57 to the passageway 59 from which it flows through the passageway into the vents 25. After entry into the vents 25 the fluid passes through the shaft to the drive train and thence to the polishing cup in the same manner as set forth with respect to the embodiment of FIG. 2.

As will be obvious to those skilled in the art to which this invention pertains, the cartridge of the emodiment of FIGS. 2 or 8 is not absolutely necessary since the fluid contained in the cartridge can be just as well contained in the chamber 18 of the body portion 16 and then a metering device such as the disc 56 can be utilized to transport a predetermined amount of fluid from the chamber to the vents of the shaft and thence through the drive train to the polishing cup.

As will be obvious from the above description, the present invention provides a number of major improvements over the existing prior art devices. Some of the more obvious improvements are the self-lubricating feature, wherein the gears no longer need to be packed in grease and therefore the instrument can be sterilized between uses; the elimination of the need to continuously dip the polishing cup into a separate supply of polishing paste and its consequent loss of time and efficiency, because now the polishing cup itself contains its own polishing abrasive; the elimination of possible burns due to lack of polishing paste, which has its cooling agent contained therein, because with the present device the cooling fluid is continuously and automatically supplied to the polishing cup whenever the cup is rotated and the elimination of the mess caused by the supplemental paste being thrown about by the rotating cup.

It is contemplated by the present invention that the fluid which serves to lubricate the driving means and provide a cooling film to the polishing cup can also serve an additional purpose in actually cleaning the teeth. Under normal conditions the teeth are cleaned by an abrasive either added to the cup or embedded therein as hereinbefore described, however it is entirely feasible to incorporate an additive into the fluid which additive would chemically remove the stains and tartar from the teeth. While almost any fluid can perform the function of cleaning to various degrees it is desirable in the present invention to utilize a fluid which is not abrasive in order that the gears in the driving means are not damaged, however such fluid must still be capable of lubricating and cooling in addition to its cleaning. One such additive is a solution of soap which in effect assists in the lubricating and also performs a cleaning function. If such a combination lubricating, cooling and cleaning fluid is used then it is entirely possible to utilize a polishing cup with no abrasive therein.

From a detailed consideration of this description, it will be apparent to those skilled in the art that this invention may be employed or constructed in a number of different ways through the use of routine skill in this field. For this reason, the present invention is not to be considered as being limited except by the appended claims defining the invention.

We claim:
1. In a dental instrument for cleaning teeth, including a hand piece and a power means, the improvement comprising:
   a polishing cup having an abrasive material embeded therein, said cup rotatively secured to said handpiece;
   driving means disposed within said handpiece and adapted to transfer energy from the power means to said polishing cup, whereby said cup is rotated when the power means is actuated, said driving means having a passageway extending therethrough in communication with the internal surface of said cup; and
   means for supplying a flow of fluid through said driving means into said cup said means comprising a pump secured to said driving means and adapted to rotate in conjunction therewith whereby fluid is drawn by said pump from a reservoir and deposited into the passageway in said driving means in communication with the internal surface of said cup, whereby the fluid lubricates said driving means and provides a cooling film to the internal surface of said cup.

2. A dental instrument in accordance with claim 1 wherein said means for supplying a fluid through said driving means into said cup comprises an interconnected passageway extending through said shaft into communication with said first and second gears and said arbor and through said arbor and said securing means into communication with the inner surface of said cup.

3. A dental instrument in accordance with claim 1 further comprising a metering member disposed between said reservoir of fluid and said means for supplying a flow of fluid whereby said metering member limits the flow of fluid from said reservoir to said supplying means.

4. A dental instrument in accordance with claim 3 wherein said metering member comprises a disc having a metering orifice therein, said disc adapted to be rotated and provide intermittent communication between said reservoir and said supplying means.

5. A dental instrument in accordance with claim 1 wherein said resevoir comprises a cartridge.

6. A dental instrument in accordance with claim 5 further comprising:
a piston slidably disposed within said cartridge; and
means for biasing said piston into said fluid, whereby said fluid is urged out of said cartridge.

* * * * *